United States Patent
Bono et al.

(10) Patent No.: US 12,408,984 B2
(45) Date of Patent: Sep. 9, 2025

(54) SURGICAL IMAGE SYSTEM AND METHOD

(71) Applicant: GLOBUS MEDICAL, INC., Audubon, PA (US)

(72) Inventors: Peter L. Bono, Bingham Farms, MI (US); James D. Lark, West Bloomfield, MI (US); John S. Scales, Ann Arbor, MI (US); Thomas J. Lord, South Milwaukee, WI (US)

(73) Assignee: Globus Medical, Inc., Audubon, PA (US)

( * ) Notice: Subject to any disclaimer, the term of this patent is extended or adjusted under 35 U.S.C. 154(b) by 1046 days.

(21) Appl. No.: 17/461,151

(22) Filed: Aug. 30, 2021

(65) Prior Publication Data

US 2022/0031395 A1  Feb. 3, 2022

Related U.S. Application Data

(63) Continuation-in-part of application No. 15/816,861, filed on Nov. 17, 2017, now Pat. No. 11,135,026.

(Continued)

(51) Int. Cl.
*A61B 34/20* (2016.01)
*A61B 8/12* (2006.01)
(Continued)

(52) U.S. Cl.
CPC ............... *A61B 34/10* (2016.02); *A61B 8/12* (2013.01); *A61B 34/20* (2016.02); *A61B 34/30* (2016.02); *A61B 90/37* (2016.02); *G06T 7/10* (2017.01); *A61B 2034/105* (2016.02); *A61B 2034/107* (2016.02); *A61B 2034/2051* (2016.02); *A61B 2090/3762* (2016.02);
(Continued)

(58) Field of Classification Search
CPC .............. A61B 90/37; A61B 2090/364; A61B 2090/378; A61B 2090/3893; A61B 2034/101; A61B 2034/107; A61B 2034/303; A61B 2034/363; A61B 2034/2051; A61B 2034/2063; A61B 5/066; A61B 34/10
See application file for complete search history.

(56) References Cited

U.S. PATENT DOCUMENTS

| | | | |
|---|---|---|---|
| 1,154,159 | A | 9/1915 | Ashworth |
| 2,557,429 | A | 6/1951 | Hawley |

(Continued)

FOREIGN PATENT DOCUMENTS

| | | |
|---|---|---|
| AR | 42807 | 7/2005 |
| AT | 370608 | 4/1983 |

(Continued)

OTHER PUBLICATIONS

Cutting Tool, Drill Bit, End Mill, Internet catalogue, http://lzqtool.com/include/search.aspx?keycode=c-grade&type=1&language-en, (Retrieved Feb. 7, 2018).

(Continued)

*Primary Examiner* — Anu Ramana

(57) ABSTRACT

A surgical system and method are provided that is configured to effect substituting a high resolution image created pre-surgery for a lower resolution image created in real time during surgery and simulating the real time position of the surgical site.

15 Claims, 4 Drawing Sheets

Related U.S. Application Data

(60) Provisional application No. 63/142,716, filed on Jan. 28, 2021, provisional application No. 62/423,677, filed on Nov. 17, 2016.

(51) Int. Cl.
*A61B 34/10* (2016.01)
*A61B 34/30* (2016.01)
*A61B 90/00* (2016.01)
*G06T 7/10* (2017.01)

(52) U.S. Cl.
CPC ............... *A61B 2090/378* (2016.02); *G06T 2207/10081* (2013.01); *G06T 2207/10136* (2013.01); *G06T 2207/30008* (2013.01)

(56) References Cited

U.S. PATENT DOCUMENTS

| | | | |
|---|---|---|---|
| 2,831,295 A | 4/1958 | Weiss | |
| 3,091,060 A | 5/1963 | Giegerich et al. | |
| 3,554,197 A | 1/1971 | Dobbie | |
| 3,577,579 A | 5/1971 | Duve et al. | |
| 4,007,528 A | 2/1977 | Shea et al. | |
| 4,008,720 A | 2/1977 | Brinckmann et al. | |
| 4,081,704 A | 3/1978 | Vassos et al. | |
| RE29,736 E | 8/1978 | Shea et al. | |
| D248,967 S | 8/1978 | Shea et al. | |
| 4,111,208 A | 9/1978 | Leuenberger | |
| 4,596,243 A | 6/1986 | Bray | |
| 4,620,539 A | 11/1986 | Andrews et al. | |
| 4,828,052 A | 5/1989 | Duran et al. | |
| 4,932,935 A | 6/1990 | Swartz | |
| 5,092,875 A | 3/1992 | McLees | |
| 5,522,829 A | 6/1996 | Michalos | |
| 5,733,119 A | 3/1998 | Carr | |
| 5,843,110 A | 12/1998 | Dross et al. | |
| 6,021,538 A | 2/2000 | Kressner et al. | |
| 6,110,174 A | 8/2000 | Nichter | |
| 6,522,906 B1 * | 2/2003 | Salisbury, Jr. ......... A61B 1/0005 600/407 | |
| 6,546,279 B1 | 4/2003 | Bova et al. | |
| 6,606,539 B2 | 8/2003 | Raab | |
| 6,635,067 B2 | 10/2003 | Norman | |
| 6,689,087 B2 | 2/2004 | Pal et al. | |
| 6,716,215 B1 | 4/2004 | David et al. | |
| 6,721,986 B2 | 4/2004 | Zhuan | |
| 6,895,305 B2 | 5/2005 | Lathan et al. | |
| 6,966,912 B2 | 11/2005 | Michelson | |
| 7,107,090 B2 * | 9/2006 | Salisbury, Jr. ......... G16H 40/63 901/14 | |
| 7,160,304 B2 | 1/2007 | Michelson | |
| 7,194,120 B2 | 3/2007 | Wicker et al. | |
| 7,346,417 B2 | 3/2008 | Luth et al. | |
| 7,660,623 B2 | 2/2010 | Hunter et al. | |
| 7,922,720 B2 | 4/2011 | May et al. | |
| 8,029,523 B2 | 10/2011 | Wallis et al. | |
| 8,038,630 B2 | 10/2011 | Pal et al. | |
| 8,170,717 B2 | 5/2012 | Sutherland et al. | |
| 8,219,178 B2 | 7/2012 | Smith et al. | |
| 8,465,491 B2 | 6/2013 | Yedlicka et al. | |
| 8,491,603 B2 | 7/2013 | Yeung et al. | |
| 8,657,821 B2 | 2/2014 | Palermo | |
| 8,728,085 B2 | 5/2014 | Marsh et al. | |
| 8,828,001 B2 | 9/2014 | Stearns et al. | |
| 8,943,634 B2 | 2/2015 | Sokol et al. | |
| 9,101,397 B2 * | 8/2015 | Guthart ............... A61B 34/30 | |
| 9,232,984 B2 * | 1/2016 | Guthart ............... A61B 34/37 | |
| 10,271,909 B2 * | 4/2019 | Guthart ............... A61B 34/37 | |
| 10,748,327 B2 * | 8/2020 | Paulson ............... G06F 30/00 | |
| 11,259,870 B2 * | 3/2022 | DiMaio ............... A61B 34/71 | |
| 11,877,897 B2 * | 1/2024 | Shelton, IV ......... A61B 90/90 | |
| 2003/0060927 A1 | 3/2003 | Gerbi et al. | |
| 2004/0050603 A1 | 3/2004 | Jaeger | |
| 2004/0147934 A1 | 7/2004 | Kiester | |
| 2005/0027397 A1 | 2/2005 | Niemeyer | |
| 2005/0043718 A1 | 2/2005 | Madhani et al. | |
| 2005/0171557 A1 | 8/2005 | Shoham | |
| 2005/0283175 A1 | 12/2005 | Tanner et al. | |
| 2006/0229624 A1 | 10/2006 | May et al. | |
| 2006/0235305 A1 | 10/2006 | Cotter et al. | |
| 2006/0235306 A1 | 10/2006 | Cotter et al. | |
| 2007/0005045 A1 | 1/2007 | Mintz et al. | |
| 2007/0021738 A1 | 1/2007 | Hasser et al. | |
| 2007/0276423 A1 | 11/2007 | Green | |
| 2007/0282344 A1 | 12/2007 | Yedlicka et al. | |
| 2007/0282345 A1 | 12/2007 | Yedlicka et al. | |
| 2008/0027449 A1 | 1/2008 | Gundlapalli et al. | |
| 2008/0061784 A1 | 3/2008 | Pal et al. | |
| 2008/0108010 A1 | 5/2008 | Wang | |
| 2008/0108991 A1 | 5/2008 | von Jako | |
| 2008/0213899 A1 | 9/2008 | Olgac | |
| 2010/0145343 A1 | 6/2010 | Johnson et al. | |
| 2010/0165793 A1 | 7/2010 | Haug | |
| 2010/0198230 A1 | 8/2010 | Shoham | |
| 2010/0249506 A1 | 9/2010 | Prisco | |
| 2010/0249786 A1 | 9/2010 | Schmieding et al. | |
| 2011/0015635 A1 | 1/2011 | Aryan | |
| 2011/0015649 A1 | 1/2011 | Anvari et al. | |
| 2011/0118708 A1 | 5/2011 | Burbank et al. | |
| 2011/0118709 A1 | 5/2011 | Burbank | |
| 2011/0118778 A1 | 5/2011 | Burbank | |
| 2011/0196404 A1 | 8/2011 | Dietz et al. | |
| 2011/0230886 A1 | 9/2011 | Gustilo et al. | |
| 2011/0295270 A1 | 12/2011 | Giordano et al. | |
| 2011/0306873 A1 | 12/2011 | Shenai et al. | |
| 2011/0313428 A1 | 12/2011 | Mohr et al. | |
| 2011/0319941 A1 | 12/2011 | Bar et al. | |
| 2012/0059392 A1 | 3/2012 | Diolaiti | |
| 2012/0186372 A1 | 7/2012 | Smith et al. | |
| 2012/0211546 A1 | 8/2012 | Shelton, IV | |
| 2012/0220831 A1 | 8/2012 | Cooper et al. | |
| 2012/0266442 A1 | 10/2012 | Rogers et al. | |
| 2013/0096540 A1 | 4/2013 | Cooper et al. | |
| 2013/0123799 A1 | 5/2013 | Smith et al. | |
| 2013/0178856 A1 | 7/2013 | Ye et al. | |
| 2013/0206441 A1 | 8/2013 | Roser et al. | |
| 2013/0244820 A1 | 9/2013 | Solomon et al. | |
| 2013/0245629 A1 | 9/2013 | Xie | |
| 2013/0296886 A1 | 11/2013 | Green | |
| 2013/0304069 A1 | 11/2013 | Bono et al. | |
| 2013/0345718 A1 | 12/2013 | Crawford et al. | |
| 2014/0051922 A1 | 2/2014 | Guthart et al. | |
| 2014/0100574 A1 | 4/2014 | Bono et al. | |
| 2014/0194894 A1 | 7/2014 | Dachs, II et al. | |
| 2014/0222003 A1 | 8/2014 | Herndon et al. | |
| 2014/0350391 A1 | 11/2014 | Prisco et al. | |
| 2014/0350571 A1 | 11/2014 | Maillet et al. | |
| 2015/0119916 A1 | 4/2015 | Dietz et al. | |
| 2016/0151120 A1 | 6/2016 | Kostrzewski et al. | |

FOREIGN PATENT DOCUMENTS

| | | |
|---|---|---|
| AU | 2011215901 | 1/2003 |
| AU | 2003200831 | 8/2004 |
| BE | 861446 | 3/1978 |
| CA | 1112970 | 11/1981 |
| CA | 2513071 | 7/2004 |
| CA | 2788918 | 8/2011 |
| CH | 610753 | 5/1979 |
| CL | 252004 | 3/2005 |
| CN | 102781349 | 11/2012 |
| DE | 2730227 | 12/1980 |
| DK | 570977 | 6/1978 |
| EP | 0148304 | 7/1985 |
| EP | 0261260 | 3/1988 |
| EP | 1571581 | 9/2005 |
| EP | 1041918 | 3/2006 |
| EP | 1581374 | 8/2006 |
| EP | 1690649 | 8/2006 |
| EP | 2533703 | 12/2012 |
| ES | 465719 | 12/1980 |
| FI | 773650 | 6/1978 |
| FR | 2374886 | 7/1978 |

(56) References Cited

FOREIGN PATENT DOCUMENTS

| | | |
|---|---|---|
| GB | 1550577 | 8/1979 |
| IT | 1081824 | 5/1985 |
| JP | 2006512954 | 4/2006 |
| JP | 4481173 | 6/2010 |
| JP | 2013519434 | 5/2013 |
| JP | S5380789 | 1/2014 |
| JP | IPS5613462 | 10/2014 |
| JP | 5826771 | 12/2015 |
| NL | 7713563 | 6/1978 |
| NO | 774411 | 6/1978 |
| WO | WO9107116 | 5/1991 |
| WO | WO0215799 | 2/2002 |
| WO | WO2004062863 | 7/2004 |
| WO | WO2007008703 | 1/2007 |
| WO | WO2009151926 | 12/2009 |
| WO | WO2011100313 | 8/2011 |
| WO | WO20122166476 | 12/2012 |
| WO | WO2014150514 | 9/2014 |
| WO | WO2015006296 | 1/2015 |
| WO | WO2015166487 | 11/2015 |

OTHER PUBLICATIONS

Tungsten Carbide Drills Mills & Burs, Internet catalogue, http://chinatungsten.com/picture-bank/tungsten-carbide-drills.html, (Retrieved Feb. 7, 2018).
MasterCut Tool Corp., Bur Series, Metric, (2018).
News & Notes, British Dental Journal, vol. 191, No. 7, pp. 410-411 (Oct. 13, 2001).
MasterCut Tool Corp., Bur Series, US, (2010).

\* cited by examiner

SURGICAL IMAGE SYSTEM AND METHOD

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 63/142,716, entitled "SURGICAL IMAGE SYSTEM AND METHOD", filed Jan. 28, 2021; also, the present invention is a Continuation-In-Part of U.S. Non-Provisional patent application Ser. No. 15/816,861, entitled "ROBOTIC SURGICAL SYSTEM", filed Nov. 17, 2017, now U.S. Pat. No. 11,135,026, which claims priority to U.S. Provisional Patent Application No. 62/423,677, entitled "ROBOTIC SURGICAL SYSTEM", filed Nov. 17, 2016. The contents of the above referenced applications are incorporated herein by reference.

FIELD OF THE INVENTION

A high resolution surgical imaging system and method for real time use during surgery.

BACKGROUND OF THE INVENTION

Surgical procedures, such as those performed on the spine, are well known in the art. The central nervous system is a vital part of the human physiology that coordinates human activity. It is primarily made up of the brain and the spinal cord. The spinal cord is made up of a bundle of nerve tissue which originates in the brain and branches out to various parts of the body, acting as a conduit to communicate neuronal signals from the brain to the rest of the body, including motor control and sensations. Protecting the spinal cord is the spinal, or vertebral, column. Anatomically, the spinal column is made up of several regions, including the cervical, thoracic, lumbar and sacral regions. Each of the vertebrae associated with the various spinal cord regions are made up of a vertebral body, a posterior arch, and transverse processes.

While most people have fully functional spinal cords, it is not uncommon for individuals to suffer some type of spinal ailment or disorder which requires some type of surgical intervention. There are many different approaches taken to alleviate or minimize severe spinal disorders. One surgical procedure commonly used is a spinal fusion technique. Several surgical approaches have been developed over the years, and include the Posterior Lumbar Interbody Fusion (PLIF) procedure which utilizes a posterior approach to access the patient's vertebrae or disc space, the Transforaminal Lumbar Interbody Fusion (TLIF) procedure which utilizes a posterior and lateral approach to access the patient's vertebrae or disc space, and the Anterior Lumbar Interbody Fusion (ALIF) which utilizes an anterior approach to access the patient's vertebrae or disc space.

In addition to the spinal implants or use of bone grafts, spinal fusion surgery often utilizes spinal instrumentation or surgical hardware, such as pedicle screws, plates, or spinal rods. Once the spinal spacers and/or bone grafts have been inserted, a surgeon places the pedicle screws into a portion of the spinal vertebrae and attaches either rods or plates to the screws as a means for stabilization while the bones fuse. Currently available systems for inserting the rods into pedicle screws can be difficult to use, particularly in light of the fact that surgeons installing these rods often work in narrow surgical fields.

Moreover, since patients can vary with respect to their internal anatomy, resulting in varying curvatures of the spine, a surgeon may not always have a linear path, or may have anatomical structures that must be maneuvered around in order to properly insert the surgical rods into the pedicle screw assemblies. In addition to requiring surgical skill, difficulty in placing the rods correctly into the pedicle screws can result in unnecessary increases in the time it takes a surgeon to complete the surgical procedure. Prolonged surgery times increase the risk to the patient. More importantly, improperly aligning the rods and pedicle screw assemblies often results in post-surgery complications for the patient and requires corrective surgical procedures.

Robotic surgery, computer-assisted surgery, and robotically-assisted surgery are terms for technological developments that use robotic systems to aid in surgical procedures. Robotically-assisted surgery was developed to help overcome the limitations of pre-existing minimally-invasive surgical procedures and to enhance the capabilities of surgeons performing open surgery.

In the case of robotically-assisted minimally-invasive surgery, instead of directly moving the instruments, the surgeon uses one of two methods to control the instruments: either a direct telemanipulator or through computer control. A telemanipulator is a remote manipulator that allows the surgeon to perform the normal movements associated with the surgery while the robotic arms carry out those movements using end-effectors and manipulators to perform the actual surgery on the patient. In computer-controlled systems, the surgeon uses a computer to control the robotic arms and its end-effectors, though these systems can also still use telemanipulators for their input. One advantage of using the computerized method is that the surgeon does not have to be present, but can be anywhere in the world, leading to the possibility for remote surgery. One drawback relates to the lack of tactile feedback to the surgeon. Another drawback relates to visualization of the surgical site. Because the surgeon may be remote or the surgery may be percutaneous, is it difficult for the surgeon to view the surgery as precisely as may be needed.

In the case of enhanced open surgery, autonomous instruments (in familiar configurations) replace traditional steel tools, performing certain actions. The main object of such smart instruments is to reduce or eliminate the tissue trauma traditionally associated with open surgery.

While robots are fully capable of repetitive tasks and work well in planned, routine settings, such environments are not always possible during a surgical procedure. In addition, robots are unintelligent in that they must be programmed to perform their functionality. However, this can be problematic when the environments they are programmed to function in are not static. As robotic systems become more prevalent in the surgical field, there exists a need for such robotic-assisted procedures to be performed safely and more intelligently, and capable of modifications in real time.

To perform such surgery, it is typical to provide an image displayed on a screen to the surgeon showing the surgical site during surgery. Such images are sonograms and of low resolution, but are real time images. Before surgery, a high resolution image of the surgical site is generated, as with magnetic resonance imaging (MRI), computerized tomography (CAT scan), x-ray or the like, so the surgeon can determine how to perform the surgery and identify risk areas. These images provide vital information. However, these imaging methods cannot be performed during surgery to provide real time high resolution imaging. Instead, it is typical to provide the real time image with ultrasound to provide a live sonogram.

SUMMARY OF THE INVENTION

The present invention provides apparatus, systems, and methods for use with robotically assisted surgery. The invention provides a system and method that will provide the surgeon with high resolution images in real time. The system and method utilize a plurality of fiducial points in the surgical site that are the same in a first high resolution image and the low resolution real time image generated during surgery, which allows enhanced viewing and tracking movement of a body structure at a surgical site. The tracked movement can be used to adjust movement of the robot and its surgical tool in real time.

Accordingly, it is an objective of the invention to provide a system for use with robotically assisted surgery.

It is a further objective of the invention to provide methods for use with robotically assisted surgery.

It is a still further objective of the invention to provide methods of performing a robotically assisted surgical procedure using one or more robots.

It is a still further objective of the invention to provide methods of performing a robotically assisted surgical procedure.

It is even a further objective of the invention to program a computer to control movements of one or more robots used in the surgery.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

DETAILED DESCRIPTION OF THE INVENTION

Figure 1:
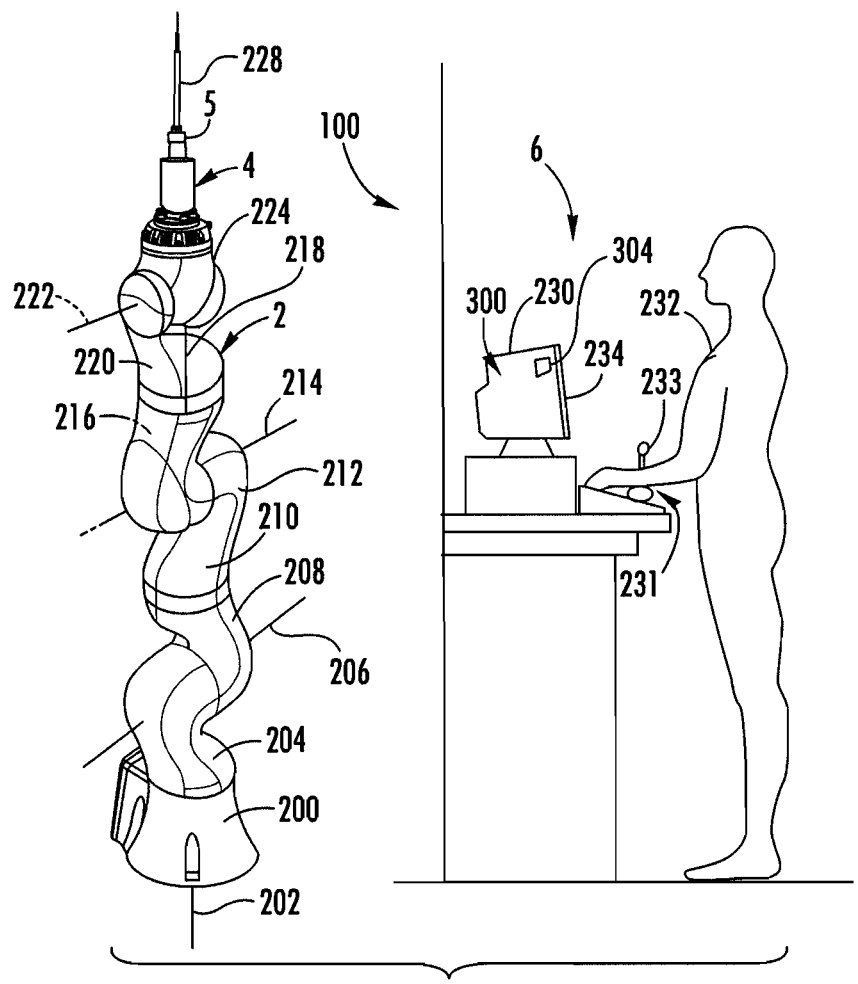
FIG. 1 is a schematic illustration of portions of a robotic surgical system.
Figure 2:
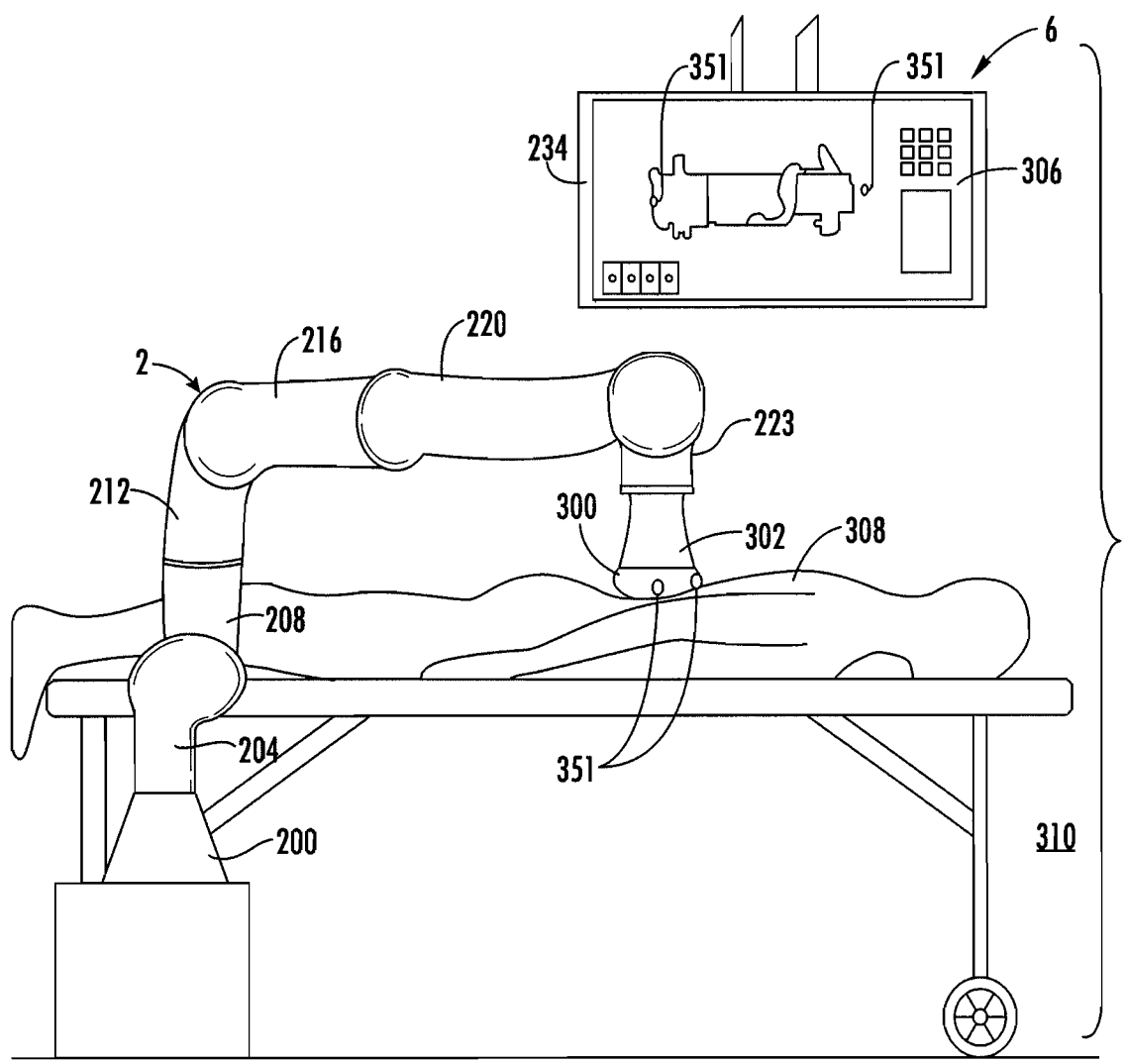
FIG. 2 is a schematic illustration of additional portions of a robotic surgical system.
Figure 3:
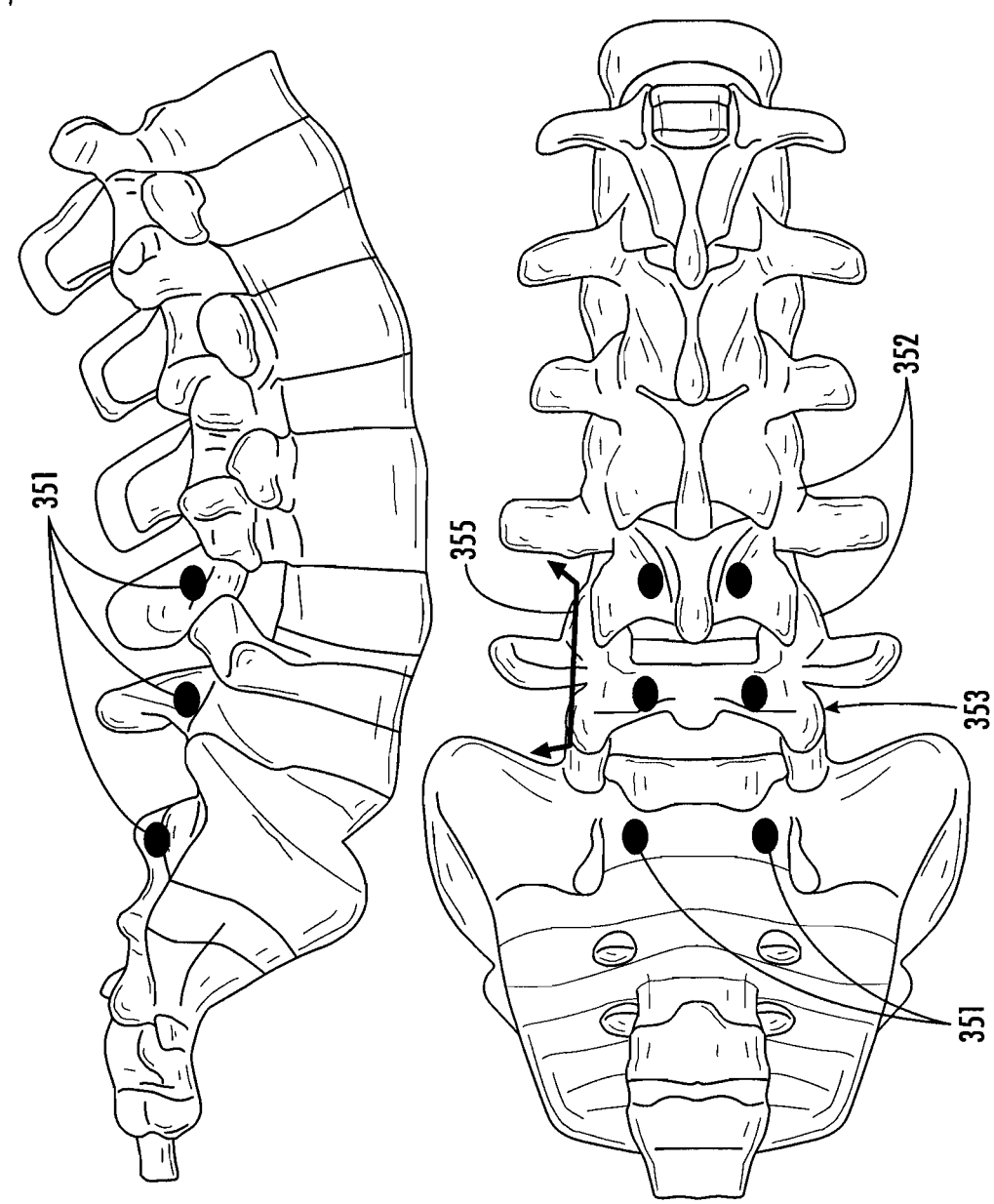
FIG. 3 is a schematic illustration of a spinal surgical site in side and plan views.
Figure 4:
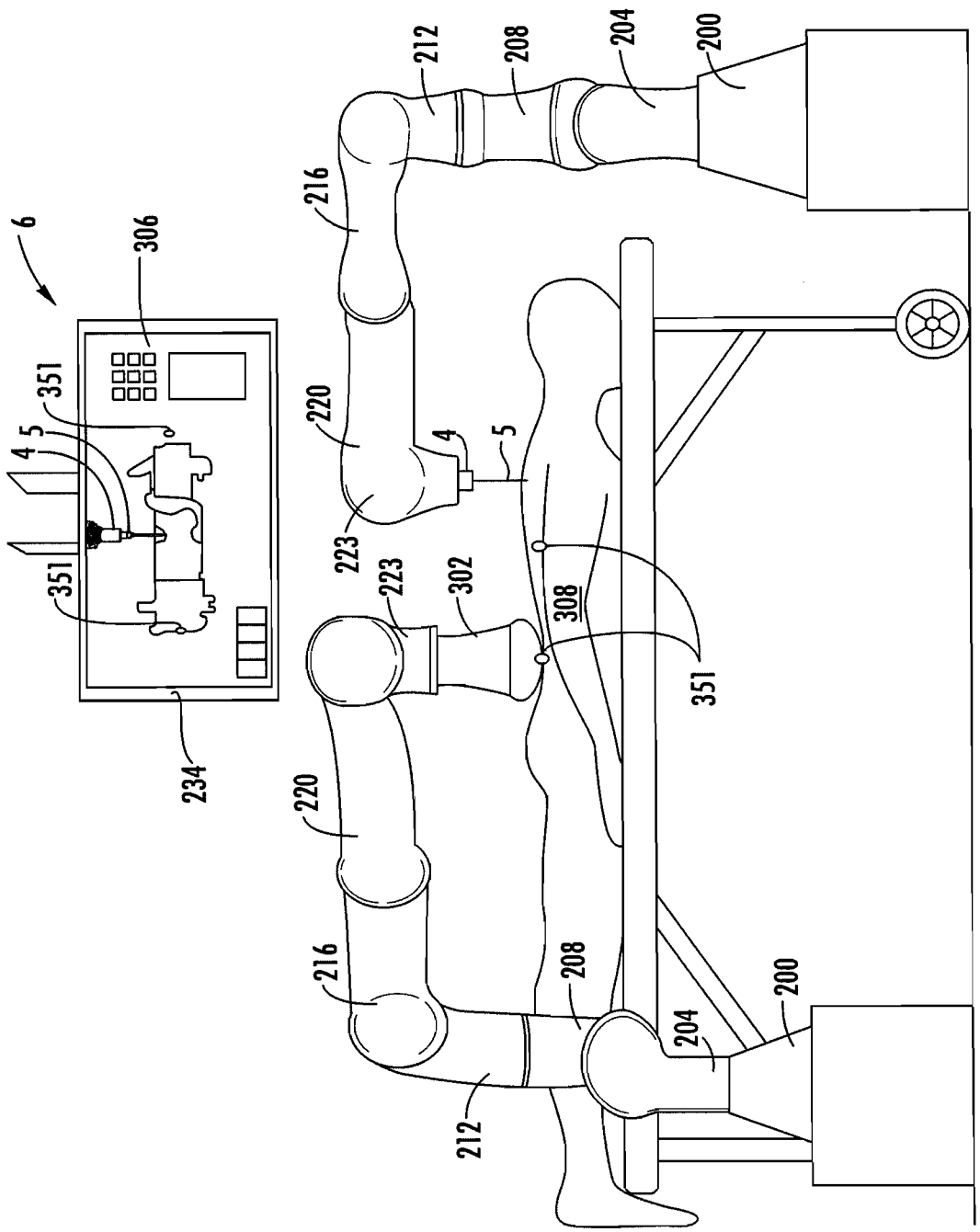
FIG. 4 is a schematic illustration of additional portions of a robotic surgical system.

Referring to FIGS. 1-3, a robotic surgical system 100 is illustrated. The robotic surgical system 100 generally includes a multi-axis robot 2, a tool 4 (surgical tool which may be an oscillating tool assembly below) with an effector 5 on a distal end thereof, and an operator station 6. The tool 4 can be of any suitable type, such as an oscillating tool and/or rotating tool. The multi-axis robot 2 includes a plurality of axes about which the oscillating tool 4 can be precisely maneuvered and oriented for surgical procedures. In a preferred, but non-limiting, embodiment, the multi-axis robot includes seven axes of movement. The axes of movement include the base axis 202, generally centered within the base 200 and about which the first arm 204 rotates. The second axis 206 is substantially perpendicular to the first, base axis 202 and about which the second arm 208 rotates. The second arm 208 includes the third axis 210 about which the third arm 212 rotates. The third arm 212 includes the fourth axis of rotation 214, which is oriented substantially perpendicular with respect to the first, base axis 202 and substantially parallel to the second axis 206. The fourth arm 216 rotates about the fourth axis 214. The fourth arm 216 includes the fifth axis 218 about which the fifth arm 220 rotates. The fifth arm 220 includes the sixth axis 222, which includes the most available rotation about the sixth axis 222 for the wrist 224 of the robot. The wrist 224 carries the tool 4 and effector 5, and has a seventh axis of rotation 228 for the cutting tool. The wrist 224 is at the distal end of the fifth arm 220. It should be noted that each axis of rotation provides an additional freedom of movement for manipulation and orientation of the tool 4. It should also be noted that while the multi-axis robot 2 is only illustrated with the tool 4, the preferred embodiment is capable of changing the effector to a variety of tools that are selectively utilized to complete a particular surgery. Drives, not shown, are utilized to move the arms into their desired positions. The drives may be electric, hydraulic or pneumatic without departing from the scope of the invention. Rotational position can be signaled to a computer 230, as with an encoder (not shown) associated with each arm 204, 208, 212, 216, 220 and other components having an axis of rotation. In the preferred embodiment, the drives are in electrical communication with the computer 230, and may further be combined with a telemanipulator, or pendant (not shown). The computer 230 can be programmed to control movement and operation of the robot(s) 2 through a manually operated controller portion 231 or autonomously through software programming. Thus, the robotic movements can be programmed by inputting code which may include positions in a two dimensional or three dimensional area or by overlaying (drawing) tool paths 355 onto an image; whereby the computer determines the proper code to cause the robot to move according to the paths drawn on the image. These tool paths 355 may be two dimensional or three dimensional without departing from the scope of the invention as shown in FIGS. 3 and 4, including drilling milling, boring and the like. The computer 230 can have a primary storage device (commonly referred to as memory) and/or a secondary storage device that can be used to store digital information, such as images described herein. Primary and secondary storage are herein referred to as storage collectively, and can include one or both primary and secondary storage. The system 100 may further include sensors positioned along various places on the multi-axis robot 2, which provide tactile feedback to the operator or surgeon 232. The computer 230 is electrically connected or coupled to the multi-axis robot 2 in a manner that allows for operation of the multi-axis robot 2, ranging from positions adjacent the robot to thousands of miles away. The computer 230 is preferably capable of accepting, retaining and executing programmed movements of the multi-axis robot 2 in a precise manner. In this manner, skilled surgeons can provide surgical care in areas, such as battlefields, while the surgeon is safe from harm's way. The controller 231 can include a movement control input device 233, such as a joy stick, keyboard, mouse or electronic screen 306, which can be touch activated. The screen 306 can be part of the monitor 234. Tool change commands can be input using the screen 306.

Referring to FIGS. 1, 2, and 4 the robotic surgical system 100 generally can include one or two multi-axis robot(s) 2, with one carrying an ultrasound imaging system 300 and one carrying an effector, such as an oscillating tool 4, both operably connected to the operator station 6 for control of operation. Typically, a surgeon 232 would utilize fluoroscopy or fluoroscopy in combination with computerized tomography (CT) scans or the like to create a high resolution image for use to evaluate surgery steps pre-surgery. Fluoroscopy images may be digitized, e.g. computerized, for viewing and storage when taken. The CT scans are performed prior to the surgery so the surgeon can identify landmarks within the patient 308. The initially created high resolution image can be either 2D or simulated 3D. In order to provide real time images to the surgeon 232 during surgery, one of the robots 2 is fitted with an ultrasound imaging probe 302 of the imaging system 300. The ultrasonic imaging probe 302 is electrically connected to an imaging system electronic controller 304 provided in the computer 230 which allows the operator to project the real-time images on the monitor 234. The patient is fitted with a plurality of fiducial point devices 351, for example, in vertebra 352 of a spine 353, prior to initial imaging to produce the high resolution image; and that image is stored in the computer 230. The initial high resolution image(s) and ultrasonic image(s) generated during surgery are stored in and recalled from the computer 230 storage and displayed on the monitor 234. The fiducial point devices 351 remain fitted to the patient in their original locations during surgery. The computer will align the real time sonogram with the initial high resolution image using the fiducial points for co-registration of the fiducial point devices 351 to effect and maintain image alignment in real time, including the scale of the images. The computer will affect display of the high resolution combined image on the monitor 234 in place of the sonogram in its current orientation and position. In some embodiments, portions of the CT image are segmented from the whole image to allow the computer to move the segmented portions to match any movement detected in the real-time images taken. This also allows the computer to alter tool paths in real-time to match the movement of the bone structure of the patient. The segmentation also allows the combined image to be rotated for addition of tool paths, screw insertion or the like to aid in programming the movements, e.g. tool paths, of the surgical robot to complete the surgery. The monitor 234 may be positioned in the operator station 6 and/or within the operating room 310. Thus, the operator can calibrate the robots positioning to correspond to the real-time ultrasonic image for completing the surgery while viewing the substituted high resolution image.

Fiducial point devices 351 can also be used to assist in determining the position of a tool 4 relative to a patient 308, and to assist in overlaying and aligning the high resolution and ultrasound images. Typically, for orthopedic surgery, fiducial point devices 351 are attached to a bone, as with a screw. Such fiducial point devices are available from Northern Digital, Inc. These devices can provide up to six degrees of monitored movement for which they provide feedback to the computer controlling the robot. In some cases, inserting more than one fiducial point device can be used to overcome interference and feedback issues that can be caused by items such as cellphones, electric motors and the like. By having redundant fiducial devices in the same bone or area of operation, one fiducial marker can be checked against the other to determine if one of the fiducial markers is sending erroneous information or failing to register movement. In this manner, electromagnetic or radio frequency sensors can be coupled with infra-red (IR) sensors or cameras to provide further cross checks to look for movement or improper positioning of the sensors.

Referring generally to the Figures, a method of monitoring the location of bones for robotic surgery includes: inserting at least one electromagnetic sensor into a bone in a manner so that the electromagnetic sensor is visible when viewed in a computer tomographic scan; taking a computerized tomographic scan of the bone and surrounding area so that the electromagnetic sensor(s) are visible in the computerized tomographic scan; storing the computerized tomographic scan on an electronic media that is computer readable; providing a surgical robot having an arm including at least two axes of movement, the robot electrically connected to a computer for controlling the movement of the robot axes, the computer having an input device for inputting commands for robot movement, the computer including a storage medium for storing and recalling electronic data; connecting a monitor to the computer to receive electrical signals therefrom for visualizing operations performed by the computer; connecting an ultrasound probe to the surgical robot; utilizing the computer input device to cause the surgical robot to move the ultrasound probe to a position to capture an image of the at least one electromagnetic sensor which may include surrounding tissues; storing the ultrasound image on the computer storage medium; causing the computer to show the computerized tomographic image on the monitor; recalling and overlaying the ultrasound image upon the computer tomographic image; and resizing the images to match each other using the electromagnetic sensor(s) visible in both images. The method may further include such features as including the step of segmenting the tomographic image and the ultrasound image so that only a portion of each image is visible on the monitor, wherein the tomographic image is segmented by a user to include bones chosen by the user, the ultrasound image segmented by the computer to match the user segmented tomographic image. The method may include the ability to rotate the segmented image on the monitor for viewing. These steps are operable from the computer which operates as an operating station for controlling operation of the robot and the image on the monitor. The images may be three dimensional images which allow the operator to overlay tool paths for the robot to follow during the surgery over the combined computer tomographic image and the ultrasound image. The image with the tool paths may then be utilized by the computer to construct electrical commands to cause the robot to move in accordance with the paths constructed by the operator. These codes may take several different forms known in the art for programming robots and computer numerical control (CNC) machining centers that operate in two dimensional and three dimensional spaces. An alternative method includes the steps of: inserting at least one electromagnetic sensor into a bone in a manner so that the electromagnetic sensor is visible when viewed in a radiographic scan; taking a computerized radiographic scan of the bone and surrounding area so that the electromagnetic sensor(s) are visible in the computerized radiographic scan; storing the computerized radiographic scan on an electronic media that is computer readable; providing a surgical robot having an arm including at least two axes of movement, the robot electrically connected to a computer for controlling the movement of the robot axes, the computer having an input device for inputting commands for robot movement, the computer including a storage medium for storing and recalling electronic data; connecting a monitor to the computer to receive electrical signals therefrom for visualizing operations performed by the computer; connecting an ultrasound probe to the surgical robot; utilizing the computer input device to cause the surgical robot to move the ultrasound probe to a position to capture an image of the at least one electromagnetic sensor which may include surrounding tissues; storing the ultrasound image on the computer storage medium; causing the computer to show the computerized radiographic image on the monitor; recalling and overlaying the ultrasound image upon the computerized radiographic image; and resizing the images to match each other using the electromagnetic sensor(s) visible in both images to assist in resizing the images. This method may further include the steps of segmenting the radiographic image and the ultrasound image so that only a portion of each image is visible on the monitor. Utilizing the segmentation of the tomographic image, a user may include bones chosen by the user, the ultrasound image segmented by the computer to match the user segmented radiographic image. The segmented image is rotatable on the monitor for viewing and overlayment of tool and cutter paths. The computer preferably operates as an operator station for controlling operation of the robot and the image on the monitor.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for monitoring the location of bones for robotic surgery comprising:

inserting at least one electromagnetic sensor into a bone;

taking a computerized tomographic scan of the bone and surrounding area so that the at least one electromagnetic sensor is visible in the computerized tomographic scan;

storing the computerized tomographic scan on an electronic media that is computer readable;

providing a surgical robot having an arm including at least two axes of movement, the robot electrically connected to a computer for controlling the movement of the robot axes, the computer having an input device for inputting commands for robot movement, the computer including a storage medium for storing and recalling electronic data;

connecting a monitor to the computer to receive electrical signals therefrom for visualizing operations performed by the computer;

connecting an ultrasound probe to the surgical robot;

utilizing the computer input device to cause the surgical robot to move the ultrasound probe to a position to capture an image of the at least one electromagnetic sensor which may include surrounding tissues;

storing the ultrasound image on the computer storage medium;

causing the computer to show the computerized tomographic image on the monitor;

recalling and overlaying the ultrasound image upon the computer tomographic image; and resizing the images to match each other using the at least one electromagnetic sensor visible in both images.

2. The method for monitoring the location of bones for robotic surgery as claimed in claim 1 including the step of segmenting the tomographic image and the ultrasound image so that only a portion of each image is visible on the monitor.

3. The method for monitoring the location of bones for robotic surgery as claimed in claim 2 wherein the tomographic image is segmented by a user to include bones chosen by the user, the ultrasound image segmented to by the computer to match the user segmented tomographic image.

4. The method for monitoring the location of bones for robotic surgery as claimed in claim 1 wherein the segmented image is rotatable on the monitor for viewing.

5. The method for monitoring the location of bones for robotic surgery as claimed in claim 1 wherein the computer is an operating station for controlling operation of the robot and the image on the monitor.

6. The method for monitoring the location of bones for robotic surgery as claimed in claim 5 wherein the operator can overlay tool paths for the robot to follow during the surgery over the combined computer tomographic image and the ultrasound image.

7. The method for monitoring the location of bones for robotic surgery as claimed in claim 6 wherein the computer constructs electrical commands to cause the robot to move in accordance with the paths constructed by the operator.

8. The method for monitoring the location of bones for robotic surgery as claimed in claim 1 wherein the computer tomographic image is a three dimensional image.

9. A method for monitoring the location of bones for robotic surgery comprising:

inserting at least one electromagnetic sensor into a bone;

taking a computerized radiographic scan of the bone and surrounding area so that the at least one electromagnetic sensor is visible in the computerized radiographic scan;

storing the computerized radiographic scan on an electronic media that is computer readable;

providing a surgical robot having an arm including at least two axes of movement, the robot electrically connected to a computer for controlling the movement of the robot axes, the computer having an input device for inputting commands for robot movement, the computer including a storage medium for storing and recalling electronic data;

connecting a monitor to the computer to receive electrical signals therefrom for visualizing operations performed by the computer;

connecting an ultrasound probe to the surgical robot;

utilizing the computer input device to cause the surgical robot to move the ultrasound probe to a position to capture an image of the at least one electromagnetic sensor which may include surrounding tissues;

storing the ultrasound image on the computer storage medium;

causing the computer to show the computerized radiographic image on the monitor;

recalling and overlaying the ultrasound image upon the computerized radiographic image; and resizing the images to match each other using the at least one electromagnetic sensor visible in both images to assist in resizing the images.

10. The method for monitoring the location of bones for robotic surgery as claimed in claim 9 including the step of segmenting the radiographic image and the ultrasound image so that only a portion of each image is visible on the monitor.

11. The method for monitoring the location of bones for robotic surgery as claimed in claim 10 wherein the tomographic image is segmented by a user to include bones chosen by the user, the ultrasound image segmented by the computer to match the user segmented radiographic image.

12. The method for monitoring the location of bones for robotic surgery as claimed in claim 9 wherein the segmented image is rotatable on the monitor for viewing.

13. The method for monitoring the location of bones for robotic surgery as claimed in claim 9 wherein the computer is an operating station for controlling operation of the robot and the image on the monitor.

14. The method for monitoring the location of bones for robotic surgery as claimed in claim 13 wherein the operator can overlay tool paths for the robot to follow during the surgery over the combined computer tomographic image and the ultrasound image.

15. The method for monitoring the location of bones for robotic surgery as claimed in claim 14 wherein the computer constructs electrical commands to cause the robot to move in accordance with the paths constructed by the operator.

\* \* \* \* \*